(12) United States Patent
Taylor et al.

(10) Patent No.: US 8,007,494 B1
(45) Date of Patent: Aug. 30, 2011

(54) DEVICE AND METHOD TO PREVENT SURGICAL BURNS

(75) Inventors: Warren Taylor, Longmont, CO (US); Richard Smoot, Jr., Arvada, CO (US); Don R. Boyle, Longmont, CO (US); David W. Newton, Longmont, CO (US)

(73) Assignee: Encision, Inc., Boulder, CO (US)

(*) Notice: Subject to any disclaimer, the term of this patent is extended or adjusted under 35 U.S.C. 154(b) by 1160 days.

(21) Appl. No.: 11/740,483

(22) Filed: Apr. 26, 2007

Related U.S. Application Data (60) Provisional application No. 60/745,850, filed on Apr. 27, 2006.

(51) Int. Cl.
*A61B 18/14* (2006.01)

(52) U.S. Cl. ............... 606/34; 606/41; 606/46

(58) Field of Classification Search .............. 606/32–34, 606/41, 42, 45–50
See application file for complete search history.

(56) References Cited

U.S. PATENT DOCUMENTS

| | | |
|---|---|---|
| 984,756 A | 2/1911 | Frisch |
| 1,754,806 A | 4/1930 | Stevenson |
| 2,004,559 A | 6/1935 | Wappler et al. |
| 2,008,367 A | 7/1935 | Rhinevault |
| 2,448,741 A | 9/1948 | Scott et al. |
| 2,741,248 A | 4/1956 | Woodhall |
| 3,070,132 A | 12/1962 | Sheridan |
| 3,580,983 A | 5/1971 | Jackson |
| 3,585,985 A | 6/1971 | Gould |
| 3,601,126 A | 8/1971 | Estes |
| 3,706,008 A | 12/1972 | Kremer |
| 3,707,149 A | 12/1972 | Hao et al. |
| 3,804,096 A | 4/1974 | Gonser |
| 3,834,392 A | 9/1974 | Lampman et al. |
| 3,838,242 A | 9/1974 | Gloucher |
| 3,895,635 A | 7/1975 | Justus et al. |
| 3,898,991 A | 8/1975 | Ikuno et al. |
| 3,905,373 A | 9/1975 | Gonser |
| 3,913,583 A | 10/1975 | Bross |
| 3,933,157 A | 1/1976 | Bjurwill et al. |
| 3,946,738 A | 3/1976 | Newton et al. |
| 3,963,856 A | 6/1976 | Carlson et al. |
| 3,974,833 A | 8/1976 | Durden |
| 3,994,287 A | 11/1976 | Turp et al. |
| 4,003,380 A | 1/1977 | Wien |
| 4,043,342 A | 8/1977 | Morrison |
| 4,084,594 A | 4/1978 | Mosior |
| 4,181,131 A | 1/1980 | Ogiu |
| 4,184,492 A * | 1/1980 | Meinke et al. .................. 606/35 |
| 4,200,104 A | 4/1980 | Harris |

(Continued)

FOREIGN PATENT DOCUMENTS

DE 1139927 8/1961

(Continued)

*Primary Examiner* — Michael Peffley
(74) *Attorney, Agent, or Firm* — Neugeboren O'Dowd PC (57) ABSTRACT

A surgical instrument and safety system comprises a safety shield having an inner surface and an outer surface, an active conductor having a first end adapted to connect with an electrode and a second end adapted to connect with an electrosurgical generator, the electrosurgical generator including contact quality monitoring circuitry, an insulator surrounding the active conductor and disposed between the active conductor and the safety shield, and a circuit interruption device in electrical communication with the safety shield. The circuit interruption device is adapted to couple to the contact quality monitoring circuitry of the electrosurgical generator and disable the flow of current to the electrode upon the occurrence of a fault condition.

28 Claims, 10 Drawing Sheets

U.S. PATENT DOCUMENTS

| | | | |
|---|---|---|---|
| 4,231,372 A | 11/1980 | Newton et al. | |
| 4,232,676 A | 11/1980 | Herczog | |
| 4,237,887 A | 12/1980 | Gonser | |
| 4,248,716 A | 2/1981 | LaValley | |
| 4,303,073 A | 12/1981 | Archibald | |
| 4,311,144 A | 1/1982 | Harada | |
| 4,325,374 A | 4/1982 | Komiya | |
| 4,343,308 A | 8/1982 | Gross | |
| 4,367,746 A | 1/1983 | Derechinsky | |
| 4,374,517 A | 2/1983 | Hagiwara | |
| 4,427,006 A | 1/1984 | Nottke | |
| 4,433,687 A | 2/1984 | Burke et al. | |
| 4,440,170 A | 4/1984 | Golden et al. | |
| 4,449,532 A | 5/1984 | Storz | |
| 4,494,541 A | 1/1985 | Archibald | |
| 4,562,838 A | 1/1986 | Walker | |
| 4,581,021 A | 4/1986 | Landau et al. | |
| 4,601,710 A | 7/1986 | Moll | |
| 4,615,330 A | 10/1986 | Nagasaki et al. | |
| 4,617,927 A | 10/1986 | Manes | |
| 4,618,885 A | 10/1986 | Nagasaki et al. | |
| 4,638,802 A | 1/1987 | Okada | |
| 4,662,369 A | 5/1987 | Ensslin | |
| 4,674,501 A | 6/1987 | Greenberg | |
| 4,716,897 A | 1/1988 | Noguchi et al. | |
| 4,719,914 A | 1/1988 | Johnson | |
| 4,744,361 A | 5/1988 | Karasawa | |
| 4,781,175 A | 11/1988 | McGreevy et al. | |
| 4,787,891 A | 11/1988 | Levin et al. | |
| 4,800,869 A | 1/1989 | Nakajima | |
| 4,818,954 A | 4/1989 | Flachenecker | |
| 4,832,048 A | 5/1989 | Cohen | |
| 4,844,063 A | 7/1989 | Clark | |
| 4,886,505 A | 12/1989 | Haynes | |
| 4,919,129 A | 4/1990 | Weber et al. | |
| 4,932,952 A | 6/1990 | Wojciechowicz | |
| 4,983,456 A | 1/1991 | Iwaskow | |
| 4,998,933 A | 3/1991 | Eggers et al. | |
| 5,009,643 A | 4/1991 | Reich et al. | |
| 5,009,656 A | 4/1991 | Reimels | |
| 5,084,045 A | 1/1992 | Helenowski | |
| 5,087,257 A | 2/1992 | Farin et al. | |
| 5,089,002 A | 2/1992 | Kirwan | |
| RE33,925 E | 5/1992 | Bales et al. | |
| 5,116,353 A | 5/1992 | Green | |
| 5,147,357 A | 9/1992 | Rose et al. | |
| 5,152,762 A | 10/1992 | McElhenney | |
| 5,176,702 A | 1/1993 | Bales et al. | |
| 5,178,620 A | 1/1993 | Eggers et al. | |
| 5,263,967 A | 11/1993 | Lyons et al. | |
| 5,275,615 A | 1/1994 | Rose | |
| 5,277,696 A | 1/1994 | Hagen | |
| 5,281,216 A | 1/1994 | Klicek | |
| 5,295,993 A | 3/1994 | Green | |
| 5,308,358 A | 5/1994 | Bond et al. | |
| 5,312,401 A * | 5/1994 | Newton et al. | 606/46 |
| 5,334,198 A | 8/1994 | Hart et al. | |
| 5,342,357 A | 8/1994 | Nardella | |
| 5,344,428 A | 9/1994 | Griffiths | |
| 5,366,443 A | 11/1994 | Eggers et al. | |
| 5,383,876 A | 1/1995 | Nardella | |
| 5,396,900 A | 3/1995 | Slater et al. | |
| 5,403,311 A | 4/1995 | Abele et al. | |
| 5,419,767 A | 5/1995 | Eggers et al. | |
| 5,423,811 A | 6/1995 | Imran et al. | |
| 5,431,638 A | 7/1995 | Hennig | |
| 5,443,463 A | 8/1995 | Stern et al. | |
| 5,496,317 A | 3/1996 | Goble et al. | |
| 5,520,685 A | 5/1996 | Wojciechowicz | |
| 5,531,676 A | 7/1996 | Edwards | |
| 5,558,671 A | 9/1996 | Yates | |
| 5,571,137 A | 11/1996 | Marlow et al. | |
| 5,599,350 A | 2/1997 | Schultz et al. | |
| 5,609,601 A | 3/1997 | Kolesa et al. | |
| 5,626,608 A | 5/1997 | Cuny et al. | |
| 5,674,220 A | 10/1997 | Fox et al. | |
| 5,683,366 A | 11/1997 | Eggers et al. | |
| 5,688,269 A | 11/1997 | Newton et al. | |
| 5,688,270 A | 11/1997 | Yates et al. | |
| 5,693,051 A | 12/1997 | Schulze et al. | |
| 5,697,281 A | 12/1997 | Eggers et al. | |
| 5,697,536 A | 12/1997 | Eggers et al. | |
| 5,697,882 A | 12/1997 | Eggers et al. | |
| 5,697,909 A | 12/1997 | Eggers et al. | |
| 5,709,680 A | 1/1998 | Yates et al. | |
| 5,720,744 A | 2/1998 | Eggleston et al. | |
| 5,731,896 A | 3/1998 | Baumann et al. | |
| 5,735,849 A | 4/1998 | Baden et al. | |
| 5,772,659 A | 6/1998 | Becker et al. | |
| 5,776,130 A | 7/1998 | Buysse et al. | |
| 5,792,141 A * | 8/1998 | Logeman | 606/46 |
| 5,797,941 A | 8/1998 | Schultz et al. | |
| 5,800,449 A | 9/1998 | Wales | |
| 5,817,093 A | 10/1998 | Williamson et al. | |
| 5,827,271 A | 10/1998 | Buysse et al. | |
| 5,833,690 A | 11/1998 | Yates et al. | |
| 5,954,686 A | 9/1999 | Garito et al. | |
| 5,976,128 A | 11/1999 | Schilling et al. | |
| 6,001,096 A | 12/1999 | Bissinger et al. | |
| 6,024,741 A | 2/2000 | Williamson et al. | |
| 6,039,732 A | 3/2000 | Ichikawa et al. | |
| 6,059,781 A | 5/2000 | Yamanashi et al. | |
| 6,086,586 A | 7/2000 | Hooven | |
| 6,174,309 B1 | 1/2001 | Wrublewski et al. | |
| 6,228,080 B1 | 5/2001 | Gines | |
| 6,228,083 B1 | 5/2001 | Lands et al. | |
| 6,238,388 B1 | 5/2001 | Ellman et al. | |
| 6,273,887 B1 | 8/2001 | Yamauchi et al. | |
| 6,398,779 B1 | 6/2002 | Buysse et al. | |
| 6,409,728 B1 | 6/2002 | Ehr et al. | |
| 6,436,096 B1 | 8/2002 | Hareyama | |
| 6,440,130 B1 | 8/2002 | Mulier et al. | |
| 6,451,018 B1 | 9/2002 | Lands et al. | |
| 6,458,130 B1 | 10/2002 | Frazier et al. | |
| 6,500,176 B1 | 12/2002 | Truckai et al. | |
| 6,506,208 B2 | 1/2003 | Hunt et al. | |
| 6,511,476 B2 | 1/2003 | Hareyama | |
| 6,582,451 B1 | 6/2003 | Marucci et al. | |
| 6,585,735 B1 | 7/2003 | Frazier et al. | |
| 6,620,157 B1 | 9/2003 | Dabney et al. | |
| 6,682,527 B2 | 1/2004 | Strul | |
| 6,682,528 B2 | 1/2004 | Frazier et al. | |
| 6,695,840 B2 | 2/2004 | Schultz | |
| 6,730,080 B2 | 5/2004 | Harano et al. | |
| 6,733,498 B2 | 5/2004 | Paton et al. | |
| 6,743,230 B2 | 6/2004 | Lutze et al. | |
| 6,767,349 B2 | 7/2004 | Ouchi | |
| 6,796,981 B2 | 9/2004 | Wham et al. | |
| 6,802,843 B2 | 10/2004 | Truckai et al. | |
| 6,827,717 B2 | 12/2004 | Brommersma | |
| 6,830,569 B2 | 12/2004 | Thompson et al. | |
| 6,855,142 B2 | 2/2005 | Harano et al. | |
| 6,890,331 B2 | 5/2005 | Kristensen | |
| 6,905,497 B2 | 6/2005 | Truckai et al. | |
| 6,929,641 B2 | 8/2005 | Goble et al. | |
| 6,929,644 B2 | 8/2005 | Truckai et al. | |
| 6,984,231 B2 | 1/2006 | Goble et al. | |
| 7,011,657 B2 | 3/2006 | Truckai et al. | |
| 7,052,496 B2 | 5/2006 | Yamauchi | |
| 7,083,618 B2 | 8/2006 | Couture et al. | |
| 7,083,619 B2 | 8/2006 | Truckai et al. | |
| 7,089,054 B2 | 8/2006 | Palti | |
| 7,090,673 B2 | 8/2006 | Dycus et al. | |
| 7,094,231 B1 | 8/2006 | Ellman et al. | |
| 7,101,371 B2 | 9/2006 | Dycus et al. | |
| 7,101,372 B2 | 9/2006 | Dycus et al. | |
| 7,101,373 B2 | 9/2006 | Dycus et al. | |
| 7,112,199 B2 | 9/2006 | Cosmescu | |
| 7,112,201 B2 | 9/2006 | Truckai et al. | |
| 7,115,121 B2 | 10/2006 | Novak | |
| 7,118,587 B2 | 10/2006 | Dycus et al. | |
| 7,131,445 B2 | 11/2006 | Amoah | |
| 7,131,971 B2 | 11/2006 | Dycus et al. | |
| 7,135,020 B2 | 11/2006 | Lawes et al. | |
| 7,147,638 B2 | 12/2006 | Chapman et al. | |
| 7,150,097 B2 | 12/2006 | Sremcich et al. | |
| 7,150,749 B2 | 12/2006 | Dycus et al. | |

| Patent No. | Date | Inventor |
|---|---|---|
| 7,153,300 B2 | 12/2006 | Goble |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,186,253 B2 | 3/2007 | Truckai et al. |
| 7,186,261 B2 | 3/2007 | Prestel |
| 7,189,233 B2 | 3/2007 | Truckai et al. |
| 7,195,631 B2 | 3/2007 | Dumbauld |
| 7,203,556 B2 | 4/2007 | Daners |
| 7,204,835 B2 | 4/2007 | Latterell et al. |
| 7,207,990 B2 | 4/2007 | Lands et al. |
| 7,211,081 B2 | 5/2007 | Goble |
| 7,211,084 B2 | 5/2007 | Goble et al. |
| 7,214,224 B2 | 5/2007 | Goble |
| 7,422,589 B2 * | 9/2008 | Newton et al. .................. 606/46 |
| 7,465,302 B2 * | 12/2008 | Odell et al. ..................... 606/34 |
| 2002/0165541 A1 | 11/2002 | Whitman |
| 2003/0073987 A1 | 4/2003 | Sakurai et al. |
| 2004/0193148 A1 | 9/2004 | Wham et al. |
| 2005/0021027 A1 | 1/2005 | Shields et al. |
| 2005/0113827 A1 | 5/2005 | Dumbauld et al. |
| 2005/0131390 A1 | 6/2005 | Heinrich et al. |
| 2005/0137590 A1 | 6/2005 | Lawes et al. |
| 2005/0187547 A1 | 8/2005 | Sugi |
| 2005/0203504 A1 | 9/2005 | Wham et al. |
| 2005/0256522 A1 | 11/2005 | Francischelli et al. |
| 2006/0079876 A1 | 4/2006 | Houser et al. |
| 2006/0129146 A1 | 6/2006 | Dycus et al. |
| 2006/0167450 A1 | 7/2006 | Johnson et al. |
| 2006/0173452 A1 | 8/2006 | Buysse et al. |
| 2006/0224158 A1 | 10/2006 | Odom et al. |
| 2006/0293656 A1 | 12/2006 | Shadduck et al. |
| 2007/0043353 A1 | 2/2007 | Dycus et al. |
| 2007/0066969 A1 | 3/2007 | McGreevy et al. |
| 2007/0078456 A1 | 4/2007 | Dumbauld et al. |
| 2007/0106297 A1 | 5/2007 | Dumbauld et al. |

FOREIGN PATENT DOCUMENTS

| | | |
|---|---|---|
| DE | 3013784 | 10/1980 |
| JP | 52-47278 | 12/1977 |
| JP | 53-13583 | 2/1978 |

* cited by examiner

DEVICE AND METHOD TO PREVENT SURGICAL BURNS

PRIORITY AND RELATED APPLICATIONS

This application claims the benefit of Provisional U.S. Patent Application No. 60/745,850 filed on Apr. 27, 2006. The details of Application No. 60/745,850 are incorporated by reference into the present application in its entirety.

FIELD OF THE INVENTION

The present invention relates to devices and methods for electrosurgical and similar procedures. In particular, but not by way of limitation, the present invention relates to systems and methods for providing an electrosurgical system with a safety device capable of deactivating the electrical current upon the occurrence of a fault condition.

BACKGROUND AND SUMMARY

Figure 1:
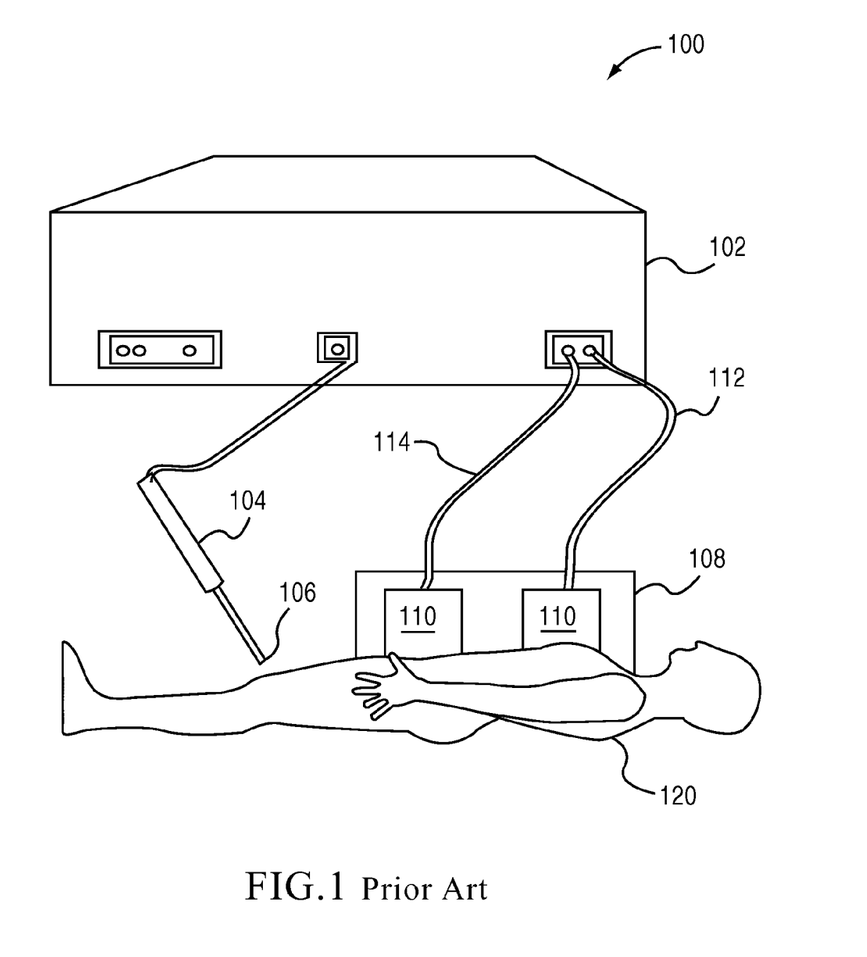
FIG. 1 is a typical electrosurgical setup shown without any monitoring of the active electrode.

Minimally invasive surgical procedures continue to experience explosive growth. Such procedures are often preferred to other more invasive procedures in that incisions are kept to a minimum size and thus such procedures facilitate shorter hospital stays and lower costs. For example, with laparoscopic surgery, a patient can return to normal activity within about one week, whereas with procedures where a large incision is made, about a month for full recovery may be required. It should be understood that hereinafter and in the claims, whenever the term "laparoscopic" is employed, similar procedures such as pelviscopic, arthroscopic, thoroscopic, and other procedures where small incisions of the foregoing type are made are also encompassed by this term. FIG. 1 described herein represents the general concept behind an electrosurgical apparatus and how it is used in a surgical setting. Referring to FIG. 1, there is illustrated an electrosurgical laparoscopic surgical system 100 including an electrosurgical tool 104 which is conventionally used to perform various surgical procedures such as ablation, incision, cauterization, etc. As is known in the laparoscopic field, a portion of the tool 104 is provided through a small incision in a patient's skin into, for example, the peritoneal cavity. The electrosurgical tool is typically provided with an active electrode probe 106 which includes an electrode and an insulative coating thereon. The tip of the probe 106 may be of different conventional shapes such as needle-shape, hook-shape, spatula-shape, graspers, scissors, etc. and serve various conventional functions such as suction, coagulation, irrigation, cutting, etc. Current is supplied to the electrosurgical tool by a generator or other electrosurgical unit 102. In order to prevent burns or other trauma to a patient 120 due to the flow of electrical current through uncontrolled paths, a return electrode 110 is placed on the patient. The return electrode 110 is then connected to the electrosurgical unit 102 via conductors 112 and 114 so that the electrical current is returned to the ESU 102 through a controlled path. While laparoscopic devices have enjoyed much success, several problems continue to present themselves.

First, if the insulation on the active electrode is damaged thereby allowing the active current (possibly in the form of arcing) to pass therethrough directly to the patient's tissue (possibly the bowel or colon), peritonitis may set in within several days. The arcing may occur out of the surgeon's field of view which may extend as little as about 2 centimeters from the tip of the active electrode (or the surgical field). The field of view is typically established by illumination and viewing sources inserted through one or more other trocar sheaths at other incisions.

Out of the field of view, there can be many centimeters of insulated active electrode which extend between the trocar sheath and the field of view. This area which is out of the field of view is potentially dangerous. Here, the insulated active electrode may come into contact with the bowel in procedures where the gall bladder, for example, is removed. If the damaged insulation and thus the attendant arcing were to occur within the field of view, the surgeon normally would immediately observe this and deactivate the generator. However, the damaged insulation can and more probably will occur at a site removed from the field of view and thus the surgeon will not be able to observe the arcing which is occurring at the bowel. Furthermore, due to the repeated insertion of the active electrode probe through the trocar sheath, the insulation thereon can be damaged especially since this accessory is quite often pushed through the trocar sheath rather roughly. Hence, damage to the active electrode insulation is particularly a problem in that the full active current may pass through the area of damaged insulation to the return electrode via an unintended site such as the bowel.

Figure 2A:
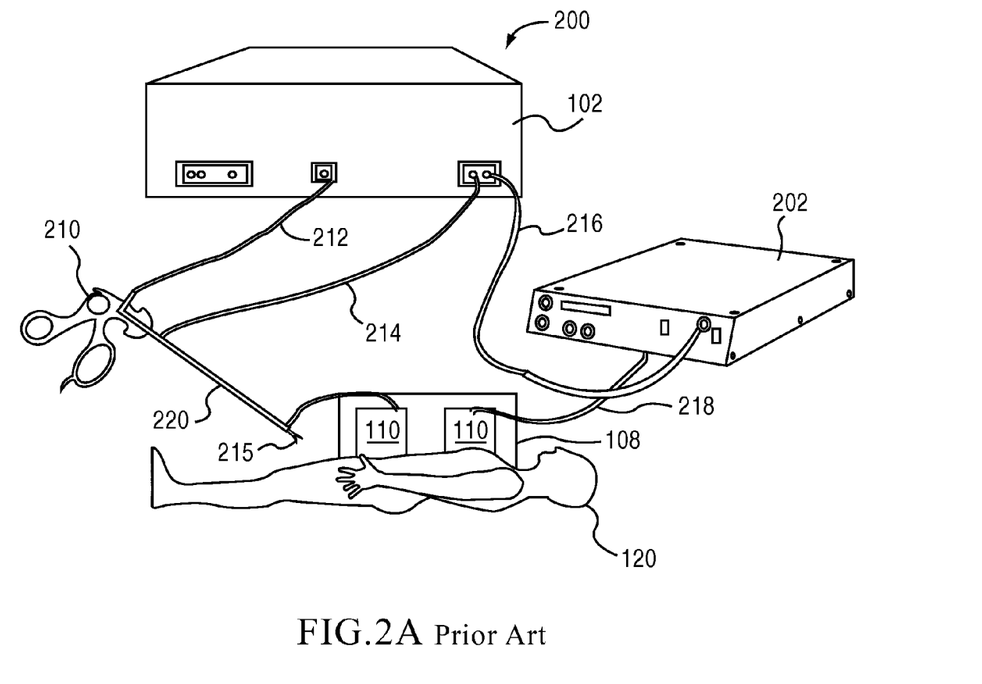
FIGS. 2A-2B show an electrosurgical setup that includes monitoring of the active electrode.
Figure 2B:
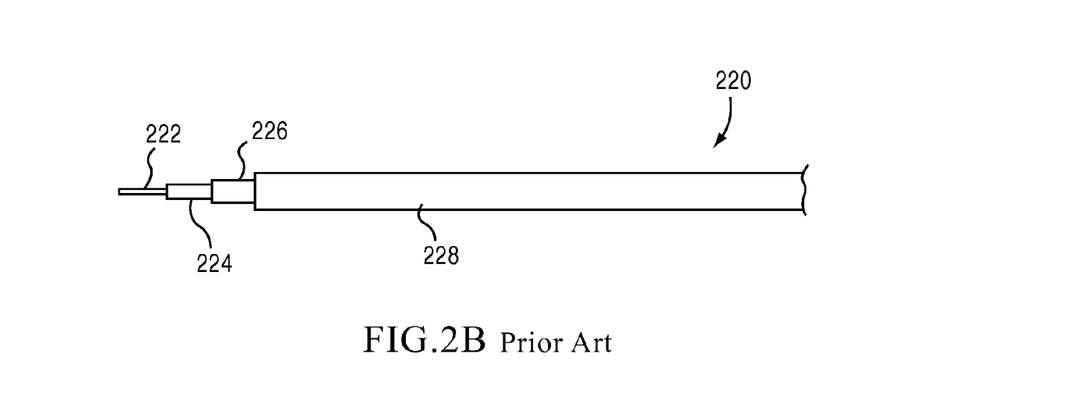

A second problem which can arise with the prior art device of FIG. 1 is caused by a capacitive effect where one electrode of the capacitance is the active electrode and the other electrode of the capacitance is the metallic trocar sheath and the dielectric between these elements is the insulation on the active electrode, as can be seen in FIG. 2B. Current from the active electrode will be capacitively coupled to the trocar sheath and then returned through the body and the return electrode to the generator. If this current becomes concentrated, for example, between the trocar sheath and an organ such as the bowel, the capacitive current can cause a burn to the organ.

A third potential problem occurs if the active electrode contacts another instrument within the peritoneal cavity such as metallic graspers or the like. The above-mentioned capacitive effect also arises in this situation where the first electrode is the active electrode and the second electrode is the metallic graspers or the like. Thus, where the graspers contact a unintended site, injury may occur.

As a first, and effective way to prevent the problems described above from presenting themselves, monitored electrosurgical tools, where a return shield is actively monitored in order to prevent unwanted current from burning or otherwise injuring a patient were developed. Systems of this type are known in the art and are exemplified by U.S. Pat. No. 5,312,401 ("the '401 patent"). The details of the '401 patent are hereby incorporated by reference in its entirety.

FIGS. 2A-3B represent a generalized representation of an AEM ("Active Electrode Monitoring") system 200 embodied by the '401 patent. This system 200 generally includes an electrosurgical generator 102 connected to a laparoscopic instrument 210 via conductors 212 and 214. The instrument 210 includes a tube assembly 220 whereby the instrument 210 provides electrical current from the generator 102 via an active electrode 215. Interposed between a patient return electrode 108 and the generator 102 is an active monitoring system 202 that monitors for one or more fault conditions in the instrument 210. FIG. 2B shows various details of the construction of the monitored instrument 220, including a metal active conductor 222, a high dielectric insulator 224, a metal shield 226, and a non-conductive outer insulating sheath 228. To render laparoscopic electrosurgical procedures more safe and thus overcome the above-mentioned problems, AEM systems such as those described in the '401 patent provide a tubular, insulated, conductive safety shield which extends at least from the trocar sheath to the field of view (that is, typically within less than two centimeters from the active electrode tip). This provides the protection which is needed with respect to the above-discussed first problem where arcing may occur at an unintended site out of the field of view.

Figure 3A:
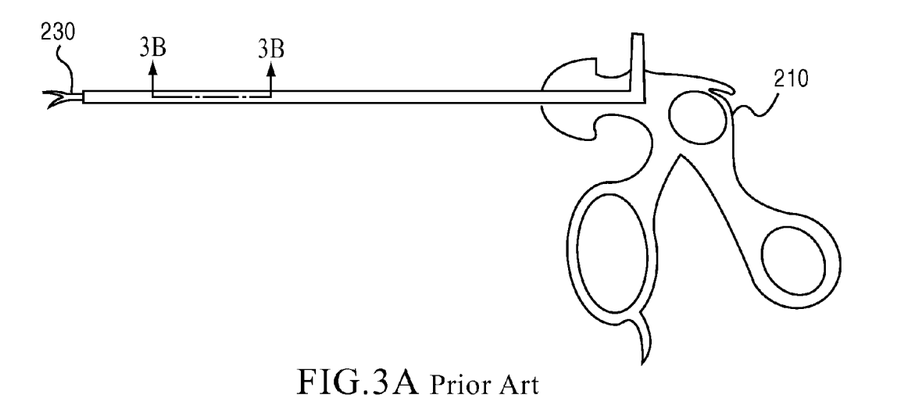
FIGS. 3A-3B show more detailed views of the electrosurgical tool in FIGS. 2A and 2B, including the details of the electrosurgical tool construction.
Figure 3B:
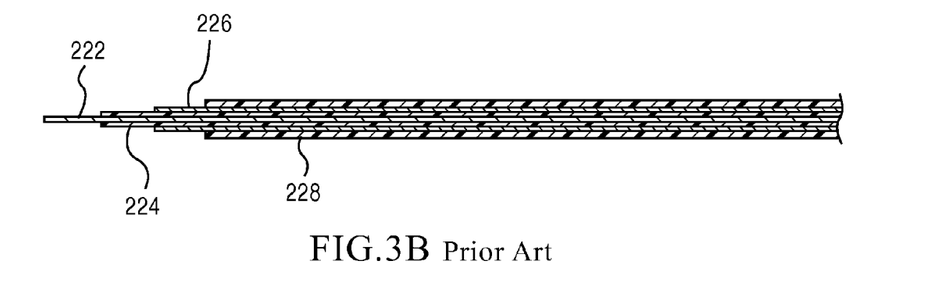

Assuming the insulation on the active electrode 222 is damaged, current will pass through the damaged insulation to the shield and then be returned to the return lead via a low impedance electrical connection between the shield and the return lead of the electrosurgical generator where the impedance should be less than about 20 ohms. A monitor circuit responsive to the shield current preferably deactivates the electrosurgical generator whenever the shield current corresponds to an abnormal condition such as an insulation breakdown. FIGS. 3A and 3B show another representation of the electrosurgical tool 210, including active electrode tip 230. Devices constructed in accordance with the '401 patent have been commercialized by Encision, Inc. of Boulder, Colo.

Despite the success obtained, and increased patient safety realized, by the inventions embodied in the '401 patent, as well as the electrosurgical tools that embody those inventions, there remain certain problems and drawbacks, as well as room for improvement.

These drawbacks include, among other things, the need for highly sophisticated and expensive electronics in addition to the actual surgical tool itself. For example, monitoring circuitry associated with these systems often includes a separate stand-alone monitor that interfaces with the electrosurgical generator. This additional piece of hardware increases total operating cost and represents an additional capital investment for a hospital or physician. Because the monitoring unit must interface with electrosurgical generators made by various manufacturers, compatibility issues may arise with traditional electrosurgical tools and systems. Finally, by requiring a separate piece of hardware, it becomes necessary to convince hospitals, doctors, and service providers to purchase a separate monitoring system for their electrosurgical needs. Modern electrosurgical generators come equipped with their own contact quality monitoring circuitry and it would be beneficial to take advantage of this existing hardware in order to provide a monitored electrosurgical tool that provides increased safety to a patient.

Thus, there is a need for a simpler way to provide a monitored electrosurgical circuit that deactivates the current source of the device when there is a fault condition or other problem. The various aspects of the present invention provide a way to benefit from the increased patient safety associated with monitored electrosurgical instruments while eliminating the above described downsides.

SUMMARY OF THE INVENTION

An instrument constructed in accordance with one or more aspects of the present invention comprises a safety shield having an inner surface and an outer surface, a layer of insulation disposed over the outer surface of the safety shield, an active conductor having a first end adapted to connect with an electrode and a second end adapted to connect with an electrosurgical generator, the electrosurgical generator including contact quality monitoring circuitry, an insulator surrounding the active conductor and disposed between the active conductor and the safety shield, and a circuit interruption device in electrical communication with the safety shield. The circuit interruption device is adapted to couple to the contact quality monitoring circuitry of the electrosurgical generator and disable the flow of current to the electrode upon the occurrence of a fault condition.

In another aspect of a device constructed in accordance with the present invention, a laparoscopic surgical instrument comprises a safety shield having an inner surface and an outer surface, a layer of insulation disposed over the outer surface of the safety shield, an active conductor having a first end adapted to connect with an electrode and a second end adapted to connect with an electrosurgical generator, the electrosurgical generator including contact quality monitoring circuitry, an insulator surrounding the active conductor and disposed between the active conductor and the safety shield, and a sensing layer in series with the contact quality monitoring circuitry of the electrosurgical generator. Preferably, the sensing layer disables the flow of current to the electrode upon the occurrence of a fault condition.

Other aspects and features of a method and device constructed in accordance with the present invention are contemplated and are more fully described in the following description and as would be known to one of skill in the art.

BRIEF DESCRIPTION OF THE DRAWINGS

Various objects and advantages and a more complete understanding of the present invention are apparent and more readily appreciated by reference to the following detailed description and to the appended claims when taken in conjunction with the accompanying drawings wherein:

DETAILED DESCRIPTION

Figure 4A:
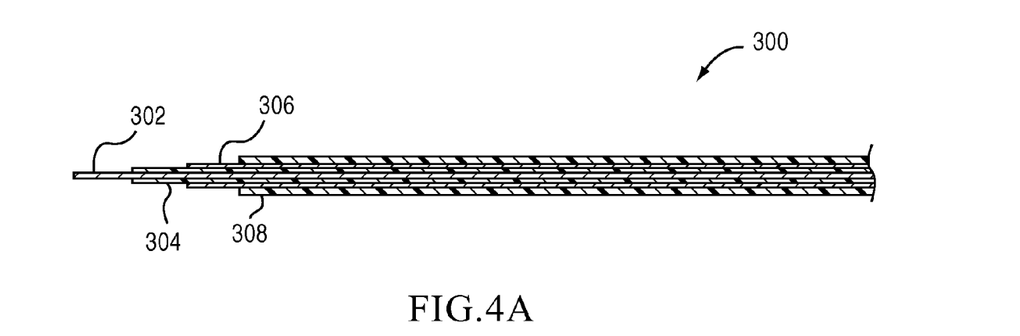
FIGS. 4A and 4B show an electrosurgical tool including one aspect of a device constructed in accordance with the present invention.
Figure 4B:
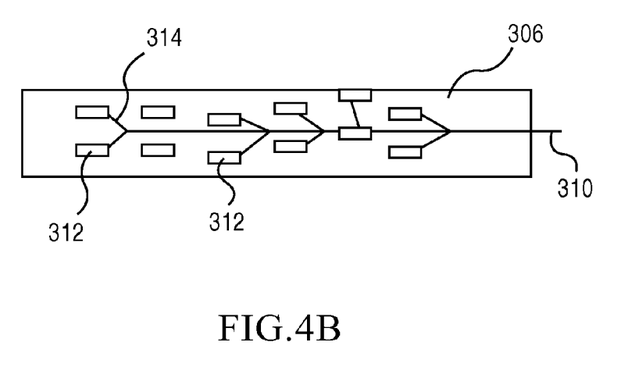

Generally, embodiments of the present invention provide the ability to monitor the current flow within an electrosurgical tool without the need for separate and/or stand-alone monitoring equipment and specialized circuitry to monitor the electrical characteristics of the current flow. Aspects of the present invention enable a monitored device by utilizing one or more techniques and structures to turn off the current flow based on a fault condition in one or more types of sensors, circuit interruption devices, or other sensing techniques that are incorporated into the electrosurgical tool, the shield within the tool or other features of the electrosurgical tool itself FIGS. 4A and 4B, illustrate a device constructed in accordance with one aspect of the present invention. A tubular assembly 300 of a laparascopic instrument is shown with the various layers of concentric materials highlighted. A metal active conductor 302 is surrounded by an insulator 304 that preferably has a high dielectric strength. A metal shield 306 surrounds the insulator 304 which is then surrounded by a non-conductive outer insulation 308. The metal shield 306 includes on its surface or embedded within its structure, one or more temperature sensors 312. The temperature sensors 312 are in turn connected to a central temperature monitoring circuit. Preferably, the central temperature monitoring circuit is directly wired to the Contact Quality Monitoring (CQM) circuit located within the existing electrosurgical generator unit. In this embodiment, the patient is protected from thermal burns by utilizing one or more temperature sensors 312 on the surface of the metal shield. The types and number of temperature sensors used can vary and may incorporate a variety of available technologies. For example, the temperature sensors may be connected in parallel as shown in FIG. 4B and interconnected by one or more conductive wires or traces 314. Types of temperature sensors include thermocouples, thermistors, resistance based sensors, and any of various other known temperature sensors. The temperature sensors 312 are preferably strategically placed around and along the shield and are adapted to monitor the shield for any rapid rise in temperature. However, any number of alternate configurations of the temperature sensors 312 are possible as would be know to one of skill in the art. All sensors are preferably tied into a central circuit 310 where any abnormal signal from the sensors would trigger an opening of one lead of the patient monitoring circuit thereby activating an alarm from the ESU (electrosurgical unit) generator. Parallel circuits are also contemplated. Preferably the patient monitoring circuit is already contained and/or integrated within the ESU generator, eliminating the need for a separate monitoring unit. The system can be set to trigger the alarm or shut off the supply of electrical current to the instrument at various temperature thresholds, depending on the particular application, equipment configuration or specific surgical procedure being performed.

Figure 5A:
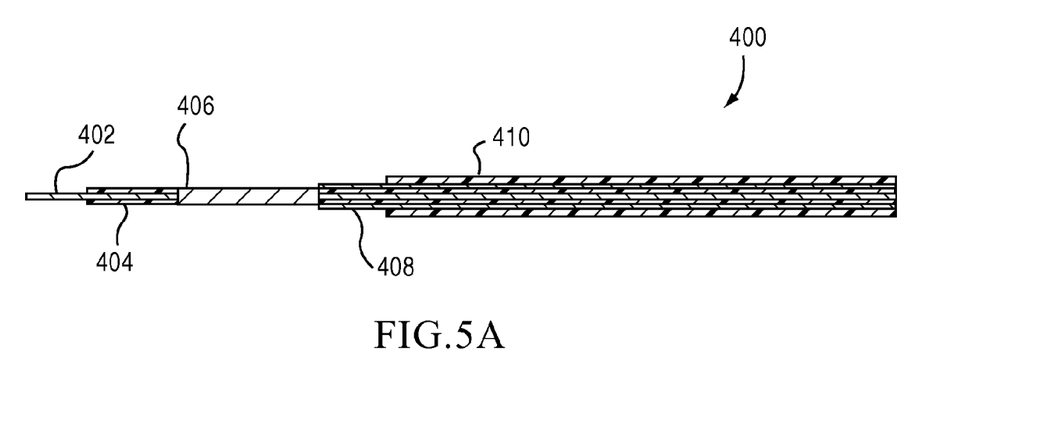
FIGS. 5A-5C show an electrosurgical tool including another aspect of a device constructed in accordance with the present invention.
Figure 5B:
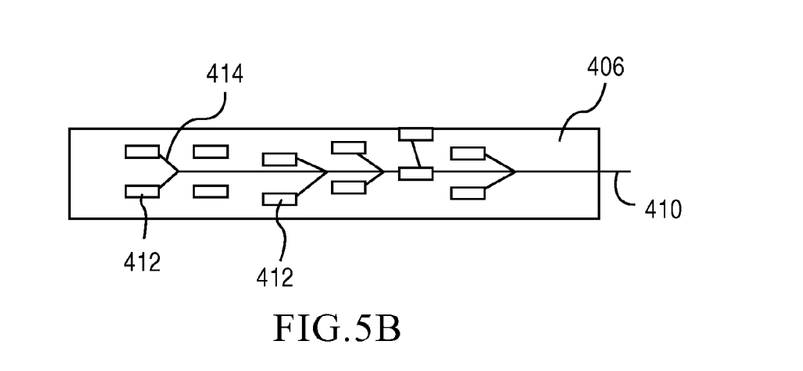
Figure 5C:
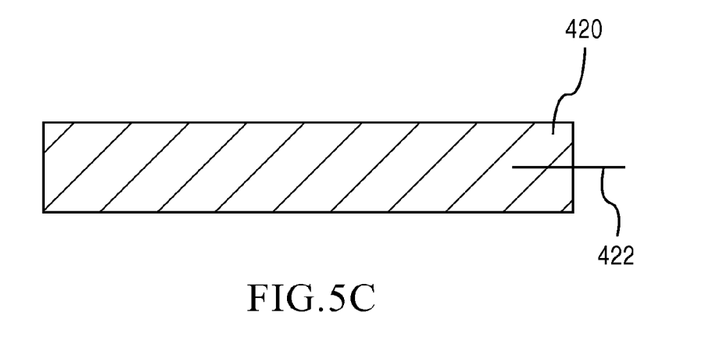

In accordance with another aspect of a device constructed in accordance with the present invention, FIGS. 5A-5C show an additional interior concentric sensing layer 406 placed on the interior of the metal shield tube 408. The sensing layer 406 preferably lies between the insulator 404 and the metal shield tube 408. The sensing layer 406 is adapted to provide the insulation and dielectric properties replacing the separate insulation layer around the active conductor. While the sensing layer 406 may be incorporated as an additional layer between the dielectric 404 and the shield 408, it may alternately be constructed and adapted to provide the same function as the dielectric insulation while simultaneously providing a sensing function.

The sensing layer 406 may be an additional layer such as a thin walled tube that contains multiple temperature sensors (such as described above in conjunction with FIGS. 4A and 4B) or one homogeneous sheet of sensing material 420 as depicted in FIG. 5C. For example, PVDF piezoelectric film sensors are available in very thin sheets or photographically etched into patterns on a polymer based sheet. This type of piezoelectric film provides an electrical signal, in the form of a current surge, when either physically flexed, exposed to a temperature change, or electrically activated. In a device constructed in accordance with an aspect of the present invention were to experience a short between the active electrode and the shield, the electrical path would cross through the film sensor. Either a temperature rise in the shield tube, thermally conducted to the thin piezo film, or an electrical current surge as the short passes through the piezo film, would alert the monitoring circuit of the short which in turn would open one leg of the CQM circuit initiating an alarm in the ESU that would stop activation of the active electrode.

In addition, the flexure or strain exerted on such a film or other sensing layer may be monitored during use, providing either feedback to the user to gauge physical characteristics of the anatomy being manipulated or additional feedback to the monitoring circuit for possible overuse that could trigger a short due to material breakage.

Figure 6A:
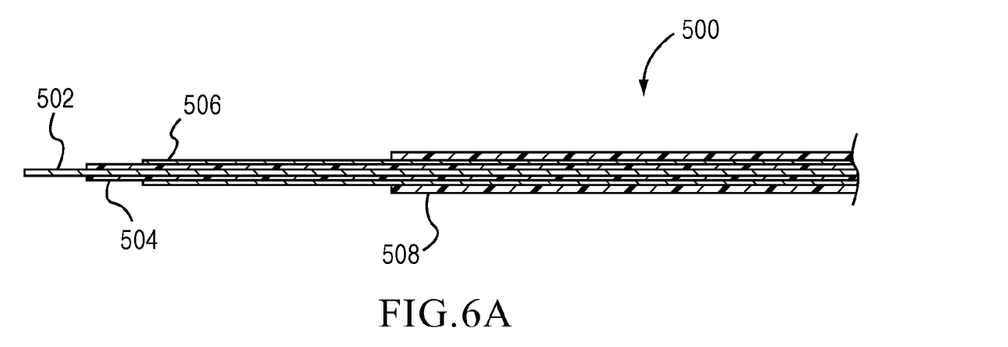
FIGS. 6A and 6B show an electrosurgical tool including another aspect of a device constructed in accordance with the present invention.
Figure 6B:
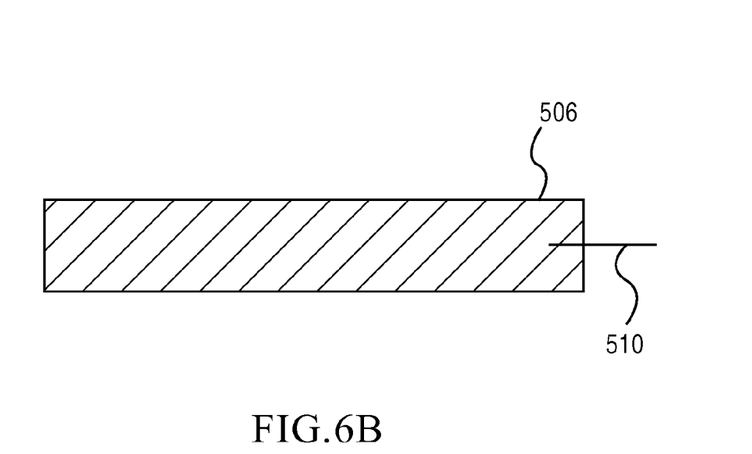

For the applications described above that rely on one or more forms of a temperature sensor, the monitoring circuit provides a trip point for opening the return electrode monitoring circuit and thereby stopping the electrical activation of the electrosurgical instrument. In both cases of temperature sensing, the monitoring circuit may be replaced with either a multiple or a single fuse. The fuse is preferably designed for maximum current based on all compatible electrosurgical generators. FIGS. 6A and 6B illustrate this concept.

In FIGS. 6A and 6B, a device 500 includes an active electrode 502, insulator 504, fuse layer 506 and outer insulation 508. The sensing layer 506 is connected to a fuse 510 and then to the CQM via a conductor to the CQM circuitry of the generator and provides a circuit interruption upon the occurrence of a fault condition in the instrument.

The concept outlined above utilizes either a series of fuses associated with each temperature sensor or a centrally located fuse that is in series with the CQM circuit. Therefore, if a set current is exceeded, the fuse blows, opening the CQM circuit and shutting down the ESU through it's own CQM monitoring circuit.

Figure 7A:
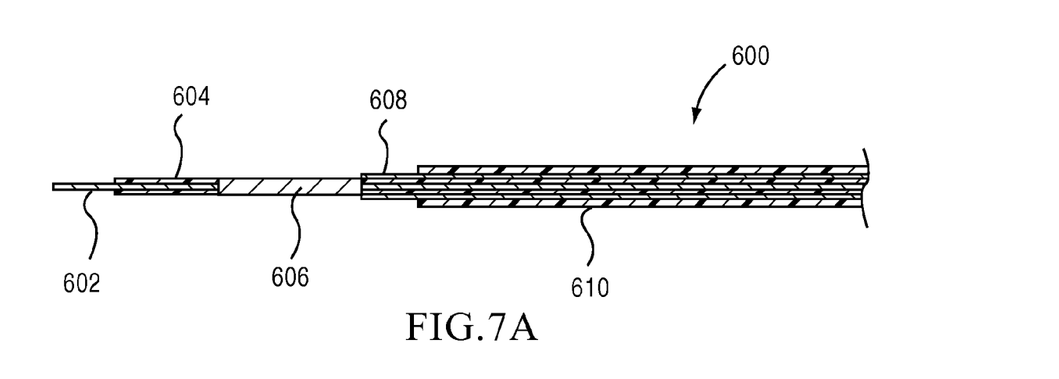
FIGS. 7A and 7B show an electrosurgical tool including another aspect of a device constructed in accordance with the present invention.
Figure 7B:
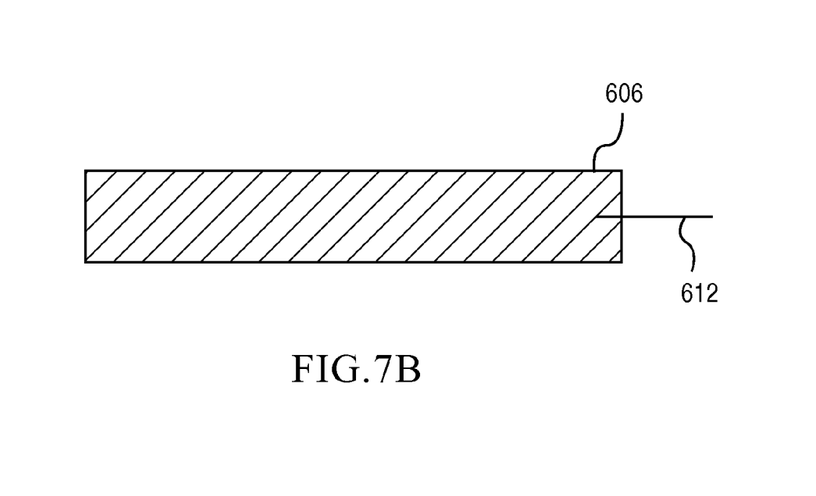
Figure 8A:
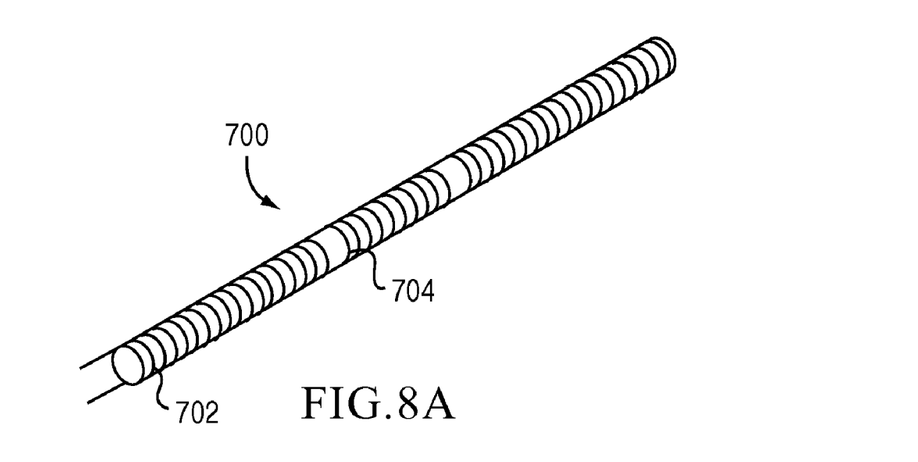
FIGS. 8A-8C show further details of the device depicted in FIG. 7.
Figure 8B:
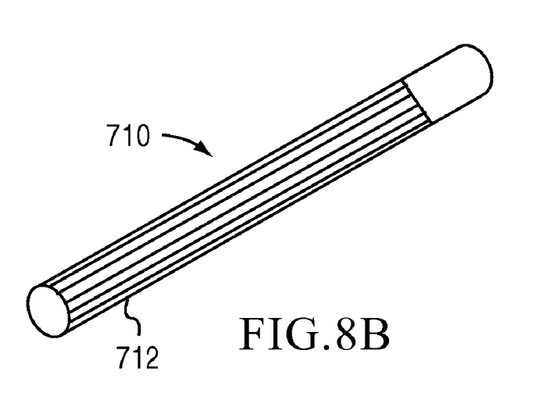
Figure 8C:
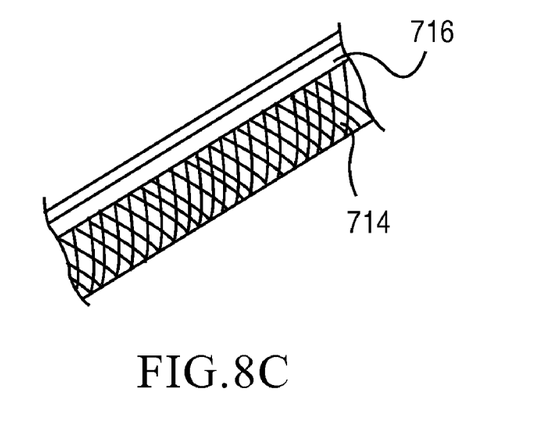
Figure 9A:
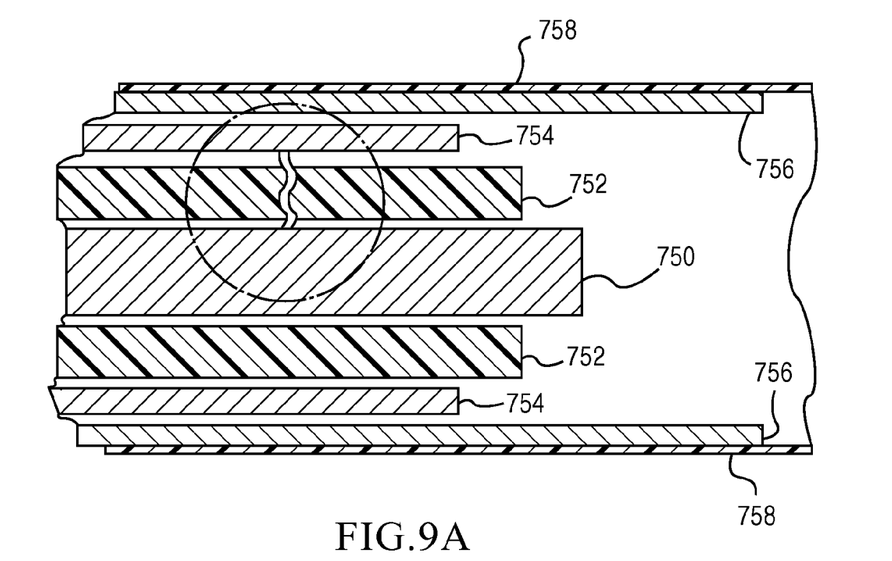
FIGS. 9A-9B show further details of the device depicted in FIG. 8.
Figure 9B:
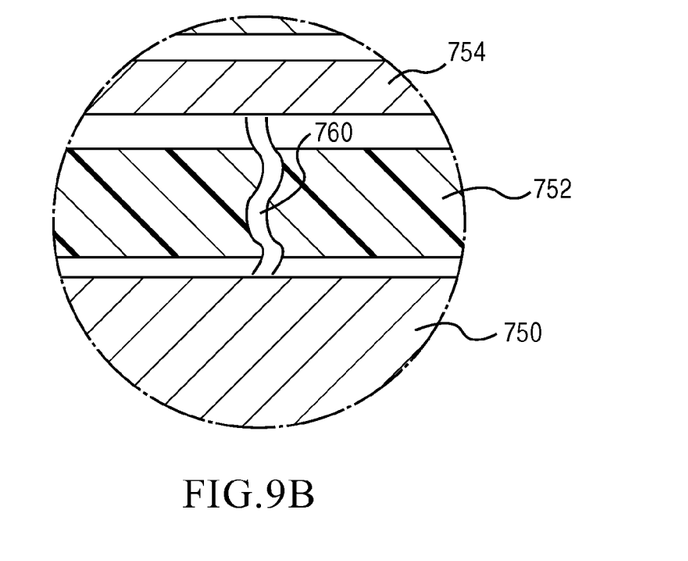

In another embodiment, and as illustrated in FIGS. 7-9, a type of thermal fuse in the form of a thin sensing layer 606 resides between the interior dielectric 604 and the outer metal shield tube 608. The sensing layer 606 surrounds the interior dielectric 604 and extends beyond the outer metal shield tube 608. The sensing layer 606 may be constructed from several different types of material but preferably has a continuous conductive trace that is connected in series via a conductor 612 with the CQM circuit of the electrosurgical generator. The trace is located either on the sensing layer's surface or interior. If a short occurs through a break in the interior dielectric 604, the electric arc would seek a path toward the closest patient reference potential which in this case is the shield circuit 606. Since the sensing layer circuit has the patient reference potential conductive trace running through it's interior, the electrical path would seek the conductive trace first, as opposed to the outer metal shield 608.

The sensing layer conductive trace 606 is preferably designed thin enough so that it would vaporize or extensively melt in a fault condition causing the shield circuit and then the CQM circuit to open. This then triggers a CQM shutdown sequence in the generator. Because the conductive trace is in series with the CQM circuit, it is preferably electrically capable of handling the normal current of the CQM circuit from both the patient pad and capacitive coupling. This current is usually under 1 amp. The trace preferably also has a low enough total resistance that it will not interfere with the patient CQM pad (return electrode). In addition, the conductive traces are preferably close enough together so as to not allow any electrical arcs to pass between the traces toward the outer shield without first breaking the sensing layer trace.

With reference to FIGS. 8A-8C, construction of the sensing layer can be accomplished by any of several techniques.

For example, as shown in FIG. 8A, a sensing layer 700 may consist of a flex circuit 702 with a continuous trace pattern 704. The pattern can be any of a zig-zag format, helix, or double helix configurations or any of many other known configurations. The flex circuit 700 can be a single sided trace or a more complex pattern of a double sided trace where the trace pattern forms a crisscrossed grid of traces nearly side-by side.

As shown in FIG. 8B, the sensing layer 710 can also be constructed by applying a metal film 712 through vapor deposition or ionic deposition techniques to a non-conductive tube. The metal deposition can be selectively applied in the final pattern desired through masking or could be achieved by machining off the metal layer in the final pattern.

As shown in FIG. 8C, an additional technique for construction of the sensing layer can be achieved by using current wire wrapped extrusions 714. A non-conductive thin walled tubing 716 can be wrapped with a double helix of copper wire then over molded with additional polymer for insulation, smoothness, and protection. While this is the preferred method due to pricing, availability, and varieties of tubing, various other means for construction of the sensing layer are contemplated.

In all examples of construction, the sensing layer may be designed thicker to also provide the same function as the interior dielectric surrounding the active electrode. In one preferred method, the sensing layer is applied on top of the dielectric insulator.

An additional property of this fusible shield is the possibility of providing full shielding of the electrical energy. This will replace the outer stainless tube currently used for shielding on many existing devices.

FIGS. 9A and 9B show a cross section of the sensing shield 754 and its orientation with respect top the active electrode 750, insulator 752, outer shield 756 and outer insulator 758. The representation of FIGS. 9A and 9B can be applied to any of the previously described sensing shield embodiments.

Figure 10A:
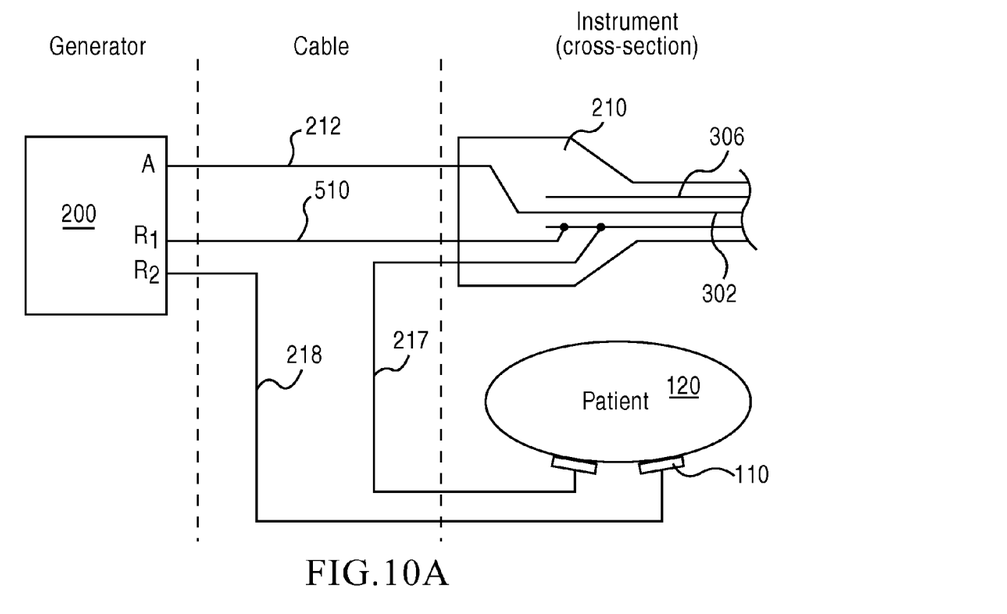
FIGS. 10A and 10B show circuit diagrams corresponding to devices constructed in accordance with one or more aspects of the present invention.
Figure 10B:
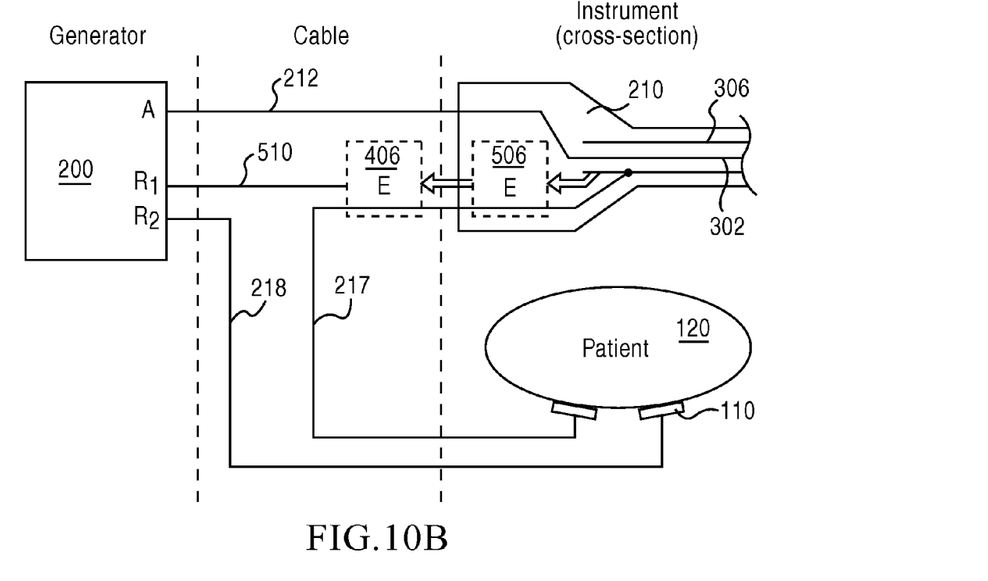

FIGS. 10A and 10B show circuit diagrams corresponding to several of the embodiments and concepts described above. In FIG. 10A, a circuit configuration is shown that corresponds to configurations where the shield fault sensing may have a direct connection to the generator CQM system. This configuration may preferably be used in connection with the fuse-based systems described above. In FIG. 10B, a circuit configuration is shown that corresponds with one or more type of electronic processing such as the previously described embodiments that incorporated temperature sensors or strain gauges. The corresponding electronics (E) may be contained within the cabling itself or within the instrument assembly. The circuit diagrams depicted in FIGS. 10A and 10B may be used with one or more of the embodiments described above and the reference numbers used are not meant to limit the use of these circuit diagrams to any particular embodiment.

A device and method constructed in accordance with various aspects of the present invention solves the foregoing problems by allowing a physician to utilize a monitored electrosurgical system without needing any special equipment setup. Namely, when compared to prior AEM systems, a device constructed in accordance with an aspect of the present invention eliminates the need for a separate AEM monitor while still providing a way to monitor the electrosurgical circuit. The system may replace instruments that the doctor is currently using and will likely be bought as a disposable product rather than capital. Because it utilizes existing hardware, it is portable between suites and hospitals. The compatibility features results in less additional education and training being needed for the physician and hospital.

Because the system is adapted to interface directly with an ESU generator rather than a separate monitor, compatibility with existing systems is further enhanced. System constructed in accordance with one or more aspects of the present invention can preferably use a common plug style that will make the attachment more universal.

Finally, because the system described above needs fewer or no complicated electronics, this technology can be incorporated more easily and for less money into competitive instruments without needing to affect their generators.

It is to be understood, however, that there is no intention to limit the invention to the forms described in the foregoing description and drawings. One skilled in the art can recognize that there are numerous modifications, equivalents and alternative constructions that fall within the spirit and scope of the invention and that are fully recognized by those of skill in the art. For example, it is contemplated that various other circuit interruption techniques as known in the art can be used in conjunction with a device and method constructed in accordance with as aspect of the present invention. The above-described embodiments and implementations are for illustration purposes only.

For example, the disclosed inventions could also open the active electrode circuit thus stopping the flow of current to the instrument independent of the ESU. The instrument could also alert the user of a fault condition through it's own internal alarm or initiate the ESU alarm by also opening the CQM circuit. By opening the active circuit independently of the ESU, the instrument can respond quicker to shutting down the current to the active electrode rather than waiting on the reaction time of the CQM circuit which varies in each ESU. Any of the above mentioned sensing methods could open the ESU active circuit through the use of a fuse, relay, or switch. In addition, any known mechanism can be used to shut off the flow of current either in the CQM circuitry or in the active circuit itself.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A laparoscopic surgical instrument comprising:
   a safety shield having an inner surface and an outer surface;
   a layer of insulation disposed over the outer surface of the safety shield;
   an active conductor having a first end adapted to connect with an electrode and a second end adapted to connect with an electrosurgical generator, the electrosurgical generator including contact quality monitoring circuitry;
   an insulator surrounding the active conductor and disposed between the active conductor and the safety shield; and
   a circuit interruption device in communication with the safety shield and adapted to couple to the contact quality monitoring circuitry of the electrosurgical generator, wherein the circuit interruption device disables the flow of current to the electrode upon the occurrence of a fault condition and wherein the circuit interruption device comprises a temperature sensor attached to the safety shield.

2. The laparoscopic instrument of claim 1 wherein the temperature sensor is in thermal communication with the safety shield.

3. The laparoscopic instrument of claim 2, wherein the temperature sensor is a discrete element.

4. The laparoscopic instrument of claim 2, wherein the temperature sensor is a homogeneous film.

5. The laparoscopic instrument of claim 4, wherein the homogeneous film further comprises a current sensor.

6. The laparoscopic in instrument of claim 1, wherein the circuit interruption device comprises a plurality of temperature sensors attached to the safety shield.

7. The laparoscopic instrument of claim 1, wherein the circuit interruption device is a layer distinct from the safety shield.

8. The laparoscopic instrument of claim 1, wherein the circuit interruption device further comprises a strain gauge.

9. The laparoscopic instrument of claim 1, wherein the circuit interruption device is embedded within the safety shield.

10. The laparoscopic instrument of claim 1, wherein the circuit interruption device is embedded within the insulator surrounding the active conductor and disposed between the active conductor and the safety shield.

11. The laparoscopic surgical instrument of claim 1, wherein the circuit interruption device is in electrical communication with the safety shield.

12. The laparoscopic surgical instrument of claim 1, wherein the circuit interruption device is coupled to the safety shield through a relay.

13. An electrosurgical instrument safety system, the safety system comprising:
- an electrosurgical generator that includes contact quality monitoring circuitry;
- an electrosurgical instrument incorporating therein a substantially tubular metal shield
- a circuit interruption device in electrical communication with the tubular metal shield and in electrical communication with the contact quality monitoring circuitry of the electrosurgical generator, the circuit interruption device adapted to disable the flow of current from the electrosurgical generator upon the occurrence of a fault condition, wherein the circuit interruption device includes a temperature sensor.

14. The safety system of claim 13 wherein the circuit interruption device includes a homogeneous film.

15. The safety system of claim 13 wherein the circuit interruption device includes a strain gauge.

16. The electrosurgical instrument safety system of claim 13, wherein the circuit interruption device is in physical communication with the tubular metal shield.

17. A laparoscopic surgical instrument comprising:
- a safety shield having an inner surface and an outer surface;
- a first insulator disposed over the outer surface of the safety shield;
- an active conductor having a first end adapted to connect with an electrode and a second end adapted to connect with an electrosurgical generator, the electrosurgical generator including contact quality monitoring circuitry;
- a second insulator surrounding the active conductor and disposed between the active conductor and the safety shield; and
- a sensing layer adapted to be in series with the contact quality monitoring circuitry of the electrosurgical generator, the sensing layer adapted to disable the flow of current to the electrode upon the occurrence of a fault condition.

18. The laparoscopic instrument of claim 17, further comprising a fuse in series with the contact quality monitoring circuitry of the electrosurgical generator.

19. The laparoscopic instrument of claim 18, wherein the fuse comprises a layer of material adapted to disrupt the flow of electricity upon the occurrence of a fault condition.

20. The laparoscopic instrument of claim 18, wherein the fuse comprises a conductive trace.

21. The laparoscopic instrument of claim 18, wherein the fuse comprises a flex circuit.

22. The laparoscopic instrument of claim 18, wherein the fuse comprises a metal film.

23. The laparoscopic instrument of claim 18, wherein the fuse comprises a current wire wrapped extrusion.

24. The laparoscopic instrument of claim 18, wherein the fuse is a layer distinct from the safety shield.

25. The laparoscopic instrument of claim 18, wherein the fuse is integrated within the safety shield.

26. The laparoscopic instrument of claim 18, wherein the fuse is a switch.

27. The laparoscopic instrument of claim 18, wherein the fuse is a relay.

28. The laparoscopic instrument of claim 18, wherein the fuse is integrated within the second insulator.

* * * * *